United States Patent [19]

Schmidt

[11] Patent Number: 5,013,302

[45] Date of Patent: May 7, 1991

[54] HYPODERMIC NEEDLE SHEATH

[75] Inventor: David A. Schmidt, Bay City, Mich.

[73] Assignee: Schmidt Industries, Inc., Bay City, Mich.

[21] Appl. No.: 456,481

[22] Filed: Dec. 26, 1989

[51] Int. Cl.⁵ .............................................. A61M 5/32
[52] U.S. Cl. .................................... 604/198; 604/220; 604/263
[58] Field of Search ............... 604/198, 263, 110, 187, 604/192, 197, 220

[56] References Cited

U.S. PATENT DOCUMENTS

| 4,655,751 | 4/1987 | Harbaugh | 604/198 |
| 4,666,435 | 5/1987 | Braginetz | 604/198 |
| 4,723,943 | 2/1988 | Spencer | 604/198 |
| 4,892,523 | 1/1990 | Haber et al. | 604/198 |

*Primary Examiner*—John D. Yasko
*Attorney, Agent, or Firm*—Learman & McCulloch

[57] ABSTRACT

A protective sheath for use with a hypodermic needle comprises a tubular body for accommodating the needle and at least a portion of the syringe barrel adjacent the needle. The body is latched in protective relation on the syringe, but may be adjusted relative to the latter to enable the needle to be exposed for use.

4 Claims, 7 Drawing Sheets

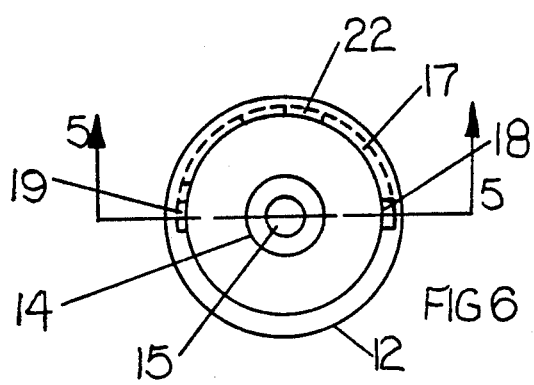
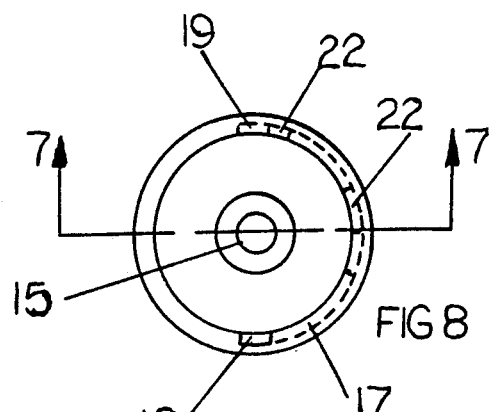
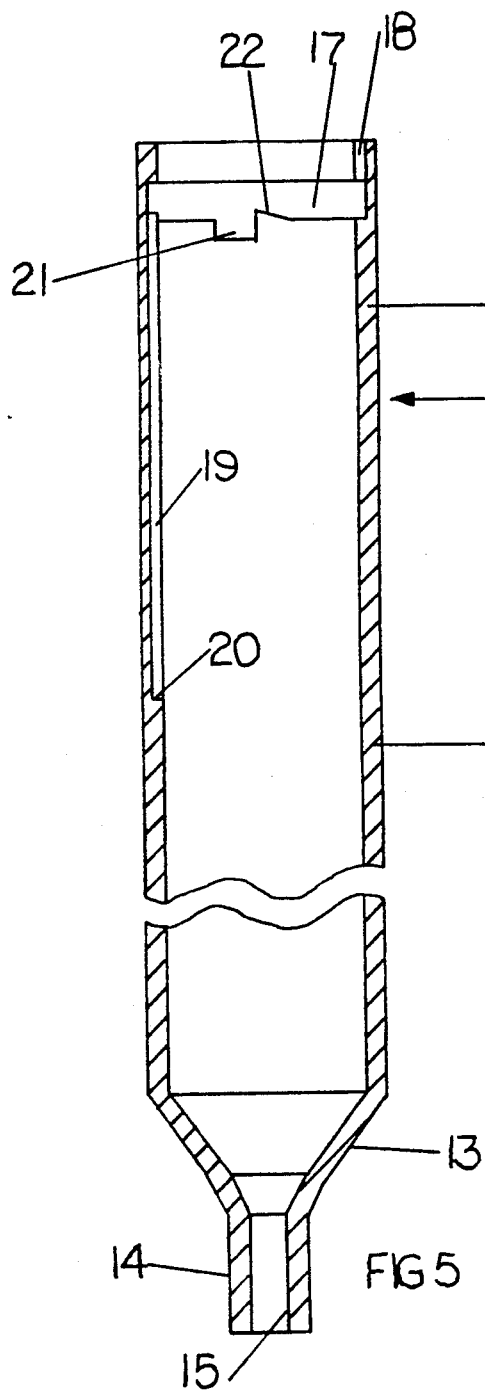
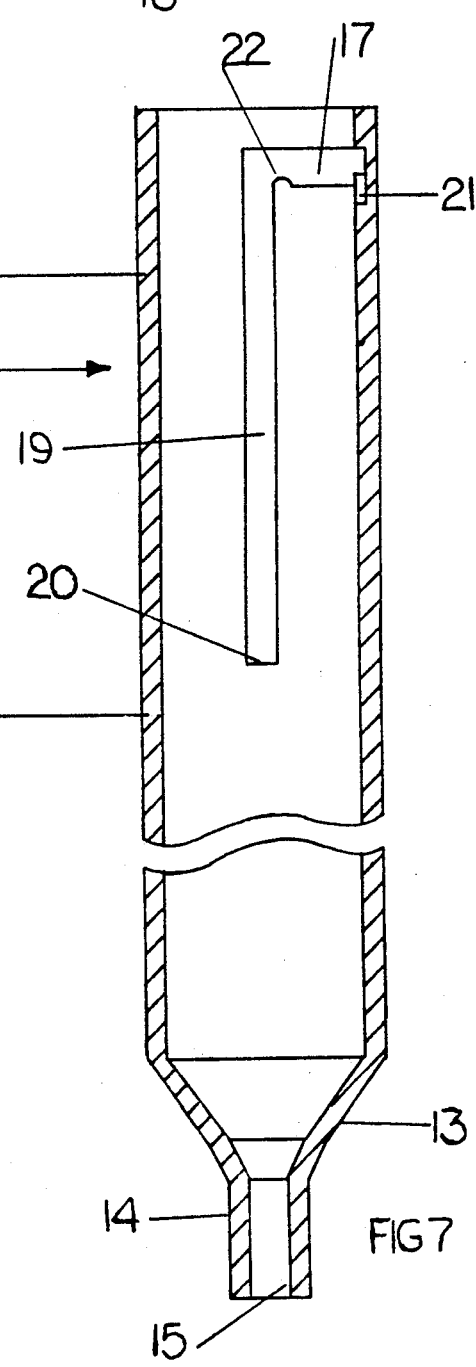

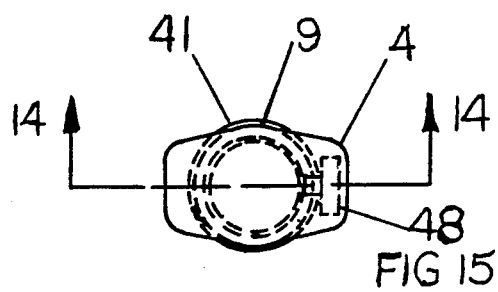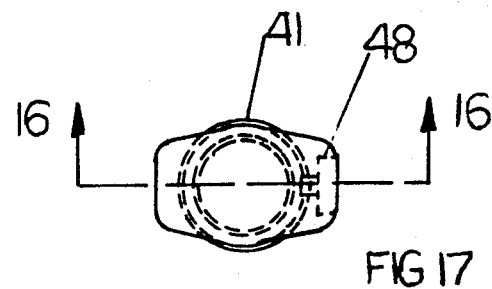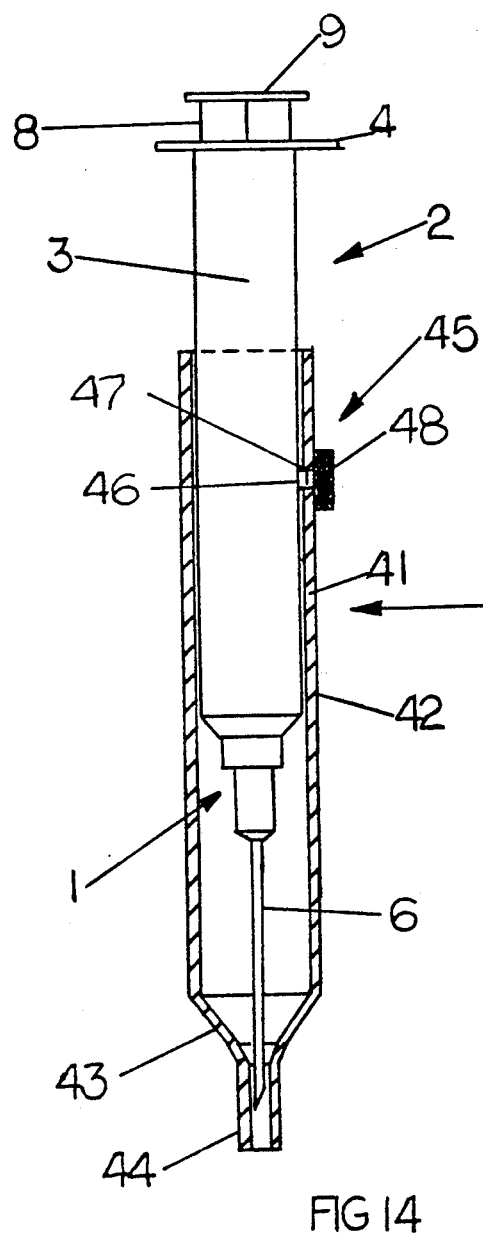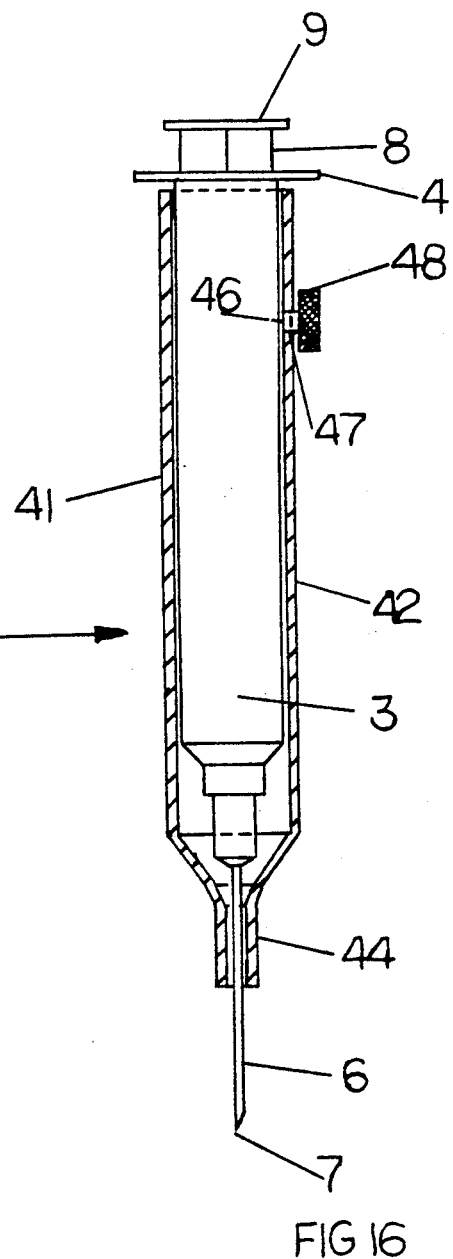

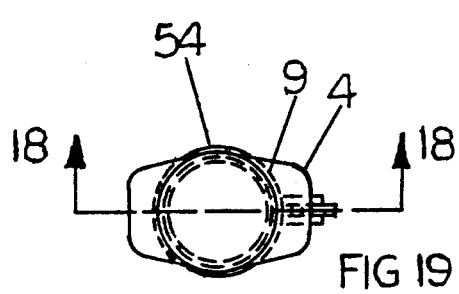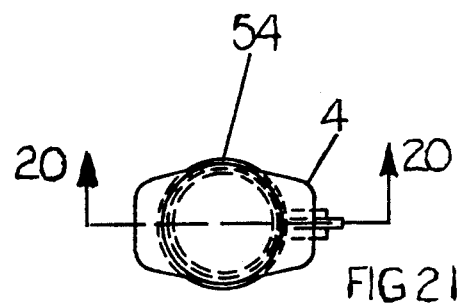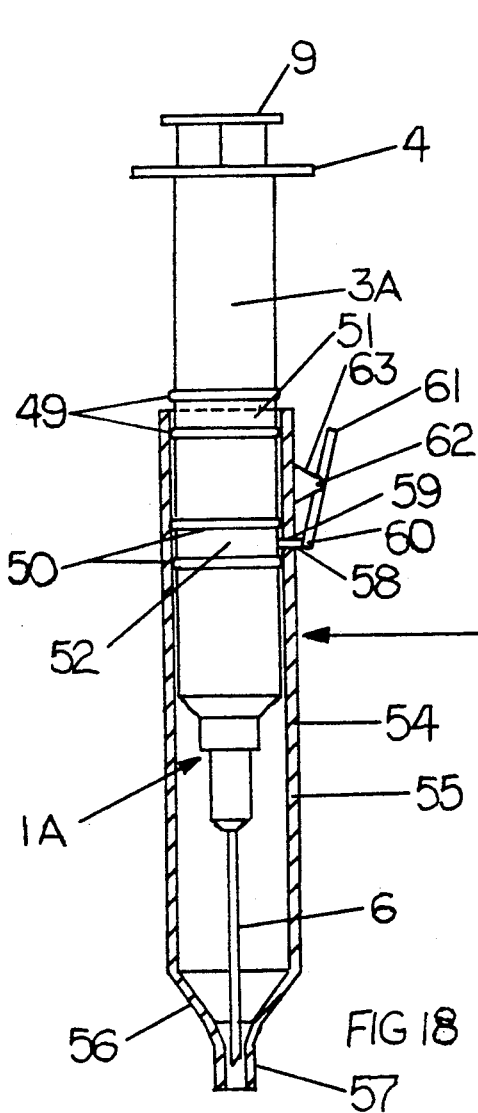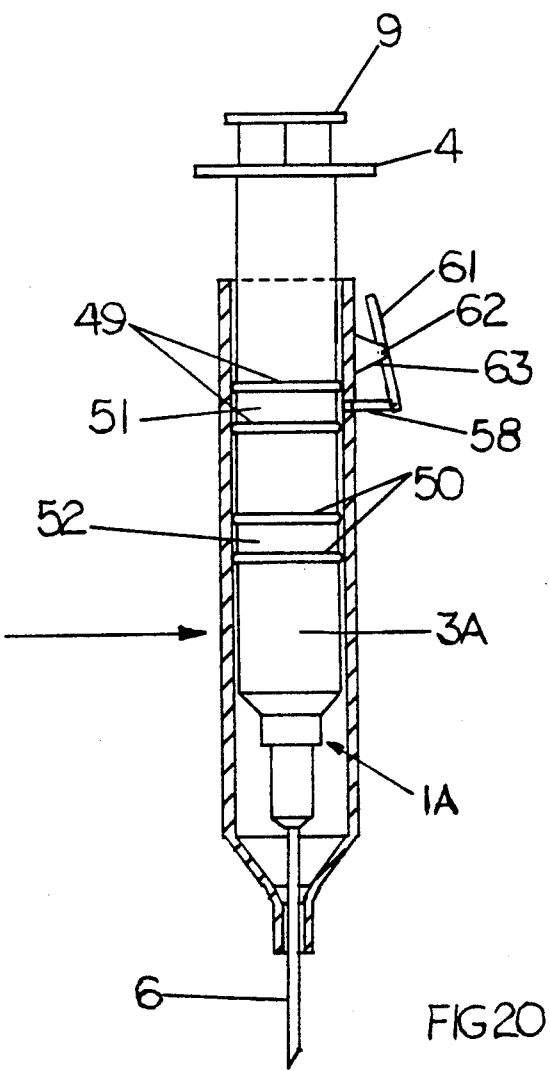

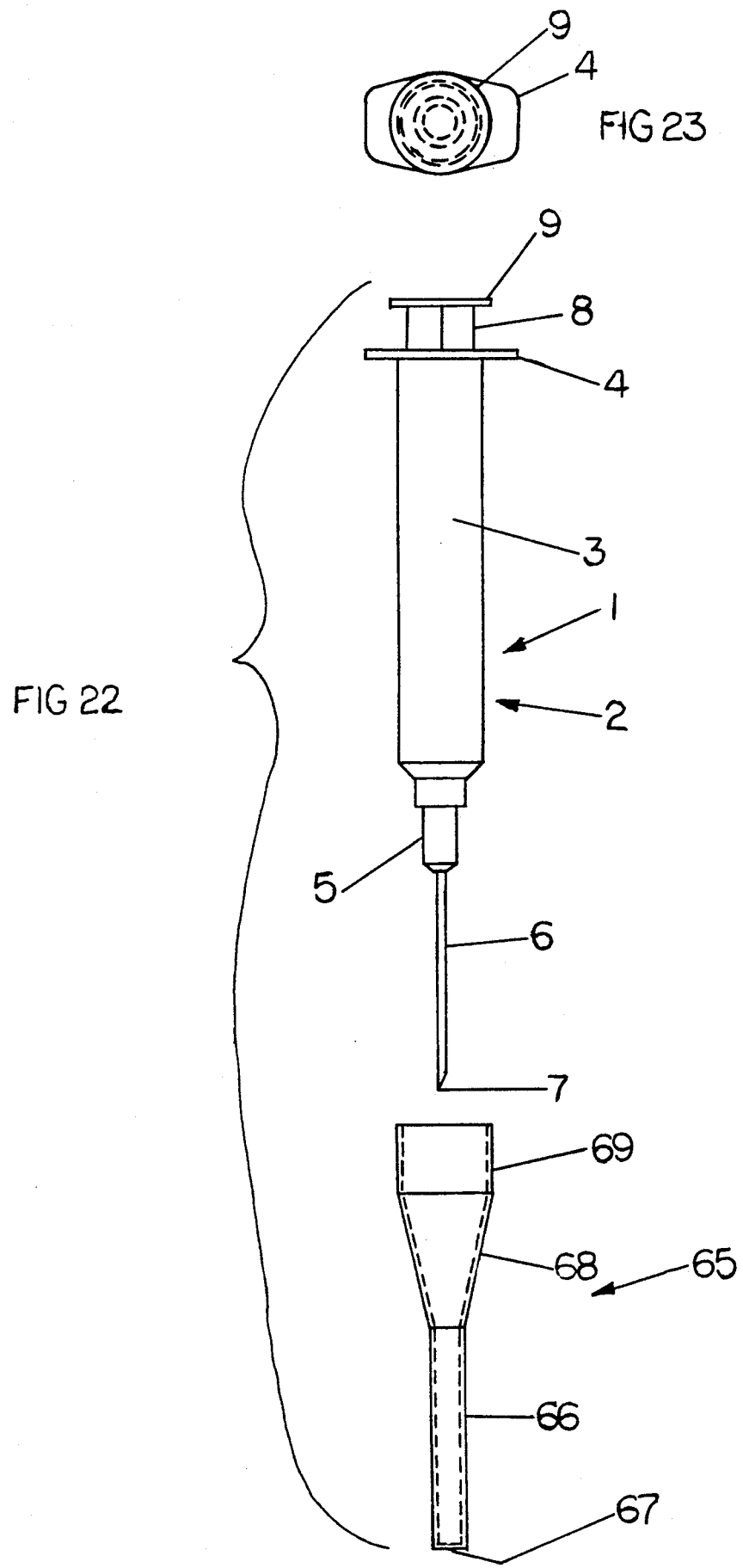

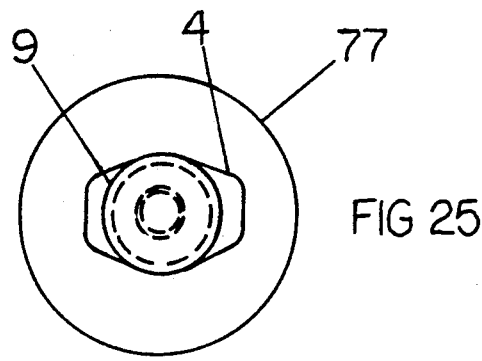
FIG 25
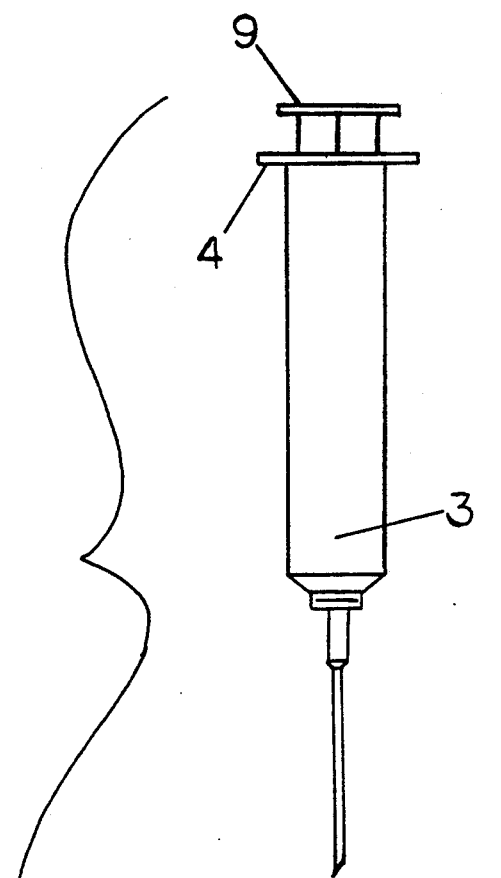
FIG 24
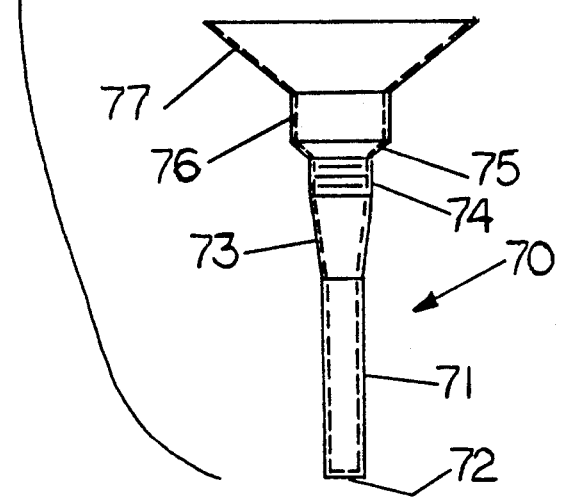

5,013,302

HYPODERMIC NEEDLE SHEATH

This invention relates to a protective sheath for a hypodermic needle which is movable from a latched, safety position in which the needle is fully encased within the sheath to a second position in which the needle is exposed for use.

BACKGROUND OF THE INVENTION

The use of hypodermic needles subjects the user to considerable risk of contracting a disease or disorder in the event the user pricks his or her finger following use of the hypodermic needle on such other person. In like manner, the person upon whom the hyprodermic needle is used by another person is subjected to the same risk if the user has a communicable disease and pricks his or her finger prior to use of the needle.

The prior art contains many proposals for protecting the users of hypodermic needles against inadvertent pricking by the needle. Some of the proposals have included flexible or collapsible covers which overlie the needle, others have included shields or guards which encircle the needle, and still others comprise pads in which the tip of the needle may be embedded. Most, if not all, of the known protective devices require manipulation of the shield or guard by the hands of the user and in such manner that the user's fingers must pass very close to the needle tip, thereby exposing the user to the risk of being pricked by the needle. The exposure to risk is increased in those instances in which the shield is flexible, or collapsible, or consists simply of a pad of spongy material.

Protective devices constructed in accordance with the invention overcome the disadvantages referred to above by utilizing relatively rigid shields of such size as to accommodate not only the entire needle, but also a substantial portion of the syringe from which the needle projects. The length of the shield and its rigidity make possible placement of the user's fingers on the shield in an area remote from the tip of the needle. The rigidity of the shield minimizes greatly the risk that the needle will penetrate the shield as the latter is applied to or removed from the syringe. Finally, the shield is latched in its protective position, thereby minimizing the possibility of inadvertent exposure of the needle.

SUMMARY OF THE INVENTION

A protective sheath for use in conjunction with a hypodermic needle comprises an elongate, tubular body formed of rigid material such as metal, polyethylene, polypropylene, or other suitable placstic, and is of such diameter as slideably to accommodate the syringe of a hypodermic needle with the needle wholly contained within the sheath. The sheath is releasably latched in its safety position from which the sheath is movable to a position in which the needle is exposed for use. In some embodiments of the invention the sheath remains assembled with the syringe regardless of whether the needle is exposed or confined within the sheath, whereas in other embodiments the sheath is removable from the syringe when the hypodermic needle is to be used to innoculate a person or withdraw fluid therefrom. In all embodiments the sheath is of sufficient rigidity to resist penetration by the needle and, correspondingly, to prevent deflection of the sheath to such an extent as to bend or otherwise damage the needle.

THE DRAWINGS

Preferred embodiments of the invention are disclosed in the accompanying drawings wherein:

FIG. 5 is an enlarged, fragmentary, sectional view taken on the line 5—5 of FIG. 6 of the sheath shown in FIG. 1;

FIG. 6 is a top plan view of the sheath shown in FIG. 5;

FIG. 7 is a sectional view similar to FIG. 5 taken on the line 7—7 of FIG. 8, but illustrating the sheath rotated clockwise through 90°;

FIG. 8 is a top plan view of the construction shown in FIG. 7;

FIG. 14 is a vertical sectional view taken on the line 14—14 of FIG. 15 illustrating a further embodiment of the invention and in which the needle is confined wholly within the sheath;

FIG. 15 is a top plan view of the apparatus shown in FIG. 14;

FIG. 16 is a sectional view taken on the line 16—16 of FIG. 17 and illustrating the hypodermic needle and sheath in adjusted positions so as to project the needle from the sheath;

FIG. 17 is a top plan view of the device shown in FIG. 16;

FIG. 18 is a sectional view taken on the line 18—18 of FIG. 19 and illustrating a further embodiment of the invention;

FIG. 19 is a top plan view of the structure shown in FIG. 18;

FIG. 20 is a sectional view taken on the line 20—20 of FIG. 21 and illustrating the apparatus of FIG. 19 in adjusted position;

FIG. 21 is a top plan view of the apparatus shown in FIG. 20;

FIG. 22 is an exploded view of a further embodiment of the invention;

FIG. 23 is a top plan view of the apparatus shown in FIG. 22;

FIG. 24 is an exploded view of a further embodiment; and

FIG. 25 is a top plan view of the apparatus shown in FIG. 24.

THE PREFERRED EMBODIMENTS

Figure 2:
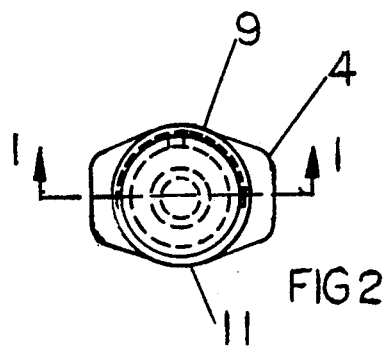
FIG. 2 is a top plan view of the embodiment shown in FIG. 1.
Figure 4:
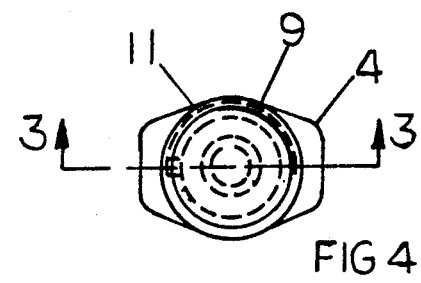
FIG. 4 is a top plan view of the construction shown in FIG. 3.

Apparatus constructed in accordance with the invention is adapted for use in conjunction with a conventional hypodermic needle 1 comprising a syringe 2 composed of a tubular barrel 3 having a discontinuous, peripheral, generally rectangular flange 4 at one end and terminating at its other end in a fitting 5 in which is secured one end of a hollow needle 6 that extends in prolongation of the syringe barrel. The needle 6 has a free end of tip 7 as is conventional. Slideably accommodated in the barrel is a reciprocable piston 8 terminating at its outer end in a thumb seat 9. The piston 8 also is rotatable within the barrel 3 and is of such diameter that movement of the piston in one direction enables the contents of the barrel to be discharged through the needle 6, whereas movement of the piston in the opposite direction enables fluid to be introduced to the barrel via the needle. As thus far described, the syringe 2, the fitting 5, and the needle 6 are conventional.

A protective, annular shield 10 formed according to the embodiment of the invention illustrated in FIGS. 1–8 comprises an elongate, tubular body 11 having an annular side wall 12 terminating at one end in a frusto-conical section 13 joined to an annular extension 14 having a passage 15 therethrough of such cross sectional area as freely to accommodate the needle 6. At its opposite end the body 11 is open. The inside diameter of the body wall 12 is of such cross sectional area as freely to accommodate the barrel 3 of the syringe 2 and the length of the body 11 is sufficient to enable the needle 6, the fitting 5, and a substantial portion of the barrel 3 to be accommodated wholly within the confines of the body 11.

The syringe 2 and the sheath 3 are provided with cooperable latching means designated generally by the reference character 16 for releasably latching the hypodermic needle 1 and the sheath 10 in at least one position of adjustment. The latching means comprises a first part or annular groove 17 formed in the inner surface of the body wall 12 adjacent the open end thereof. The groove 11 extends circumferentially through about 180°. One end of the groove 17 communicates with an axial groove 18 which extends to the free end of the body wall 12 and the opposite end of the groove 17 communicates with an axial groove 19 which extends from the groove 17 toward the opposite end of the body and terminates in a shoulder 20. Between its ends the groove 17 communicates with a keeper notch 21 which extends axially of the body 11 a short distance away from the open end thereof. Adjacent the notch 21 is a riser 22 which lies between the axial slot 18 and the notch 21.

The cooperable latch means 16 also includes a second part or projection 23. The projection 23 is of such size as to slide freely through the axial slot 18, the circumferential groove 17, and the axial groove 19. It also is of such size as freely to be accommodated within the notch 21. The axial height of the projection 23 is sufficiently less than the axial height of the circumferential groove 17 as to provide some resistance to movement of the projection 23 past the riser 22, but the projection 23 is not of such height as to preclude its movement past the riser.

Figure 1:
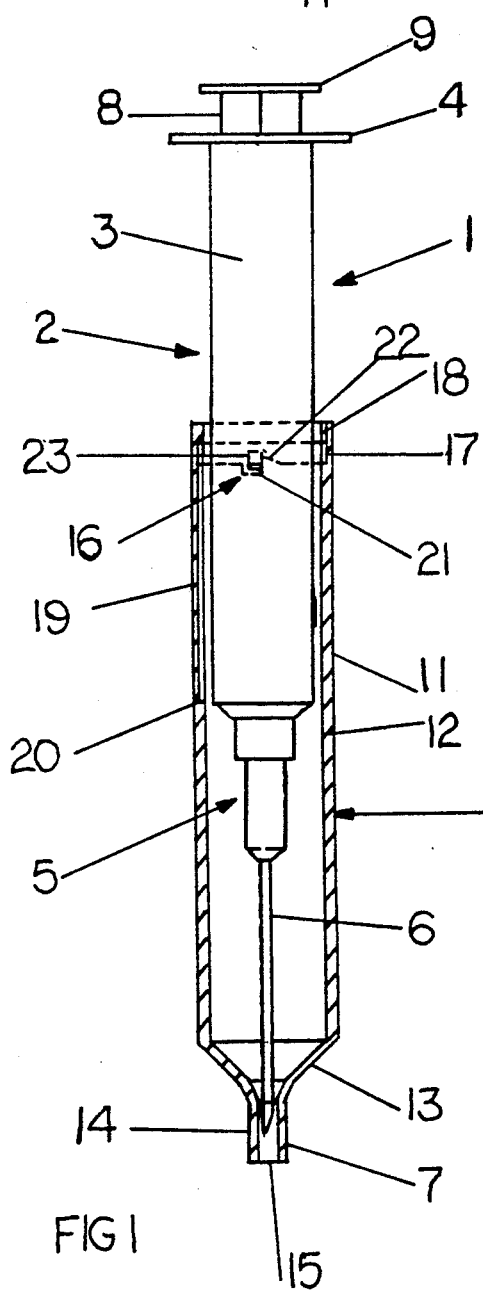
FIG. 1 is a vertical sectional view taken on the line 1—1 of FIG. 2 of a hypodermic needle and protective sheath formed in accordance with one embodiment of the invention.

In the positions of the parts shown in FIG. 1, the projection 23 extends radially of the syringe body into the relieved area provided by the peripheral groove 17 and is in register with the notch 21. The riser 22 lies in the path of movement of the projection 23 toward the axial groove 18, thereby preventing inadvertent withdrawal of the hypodermic needle through the open end of the sheath body 12. If, in this position of the projection 23, the hypodermic needle is moved axially downward, as viewed in FIG. 1, the projection 23 will seat in the notch 21, thereby preventing inadvertent relative rotation of the hypodermic needle 1 and the sheath 10.

Figure 3:
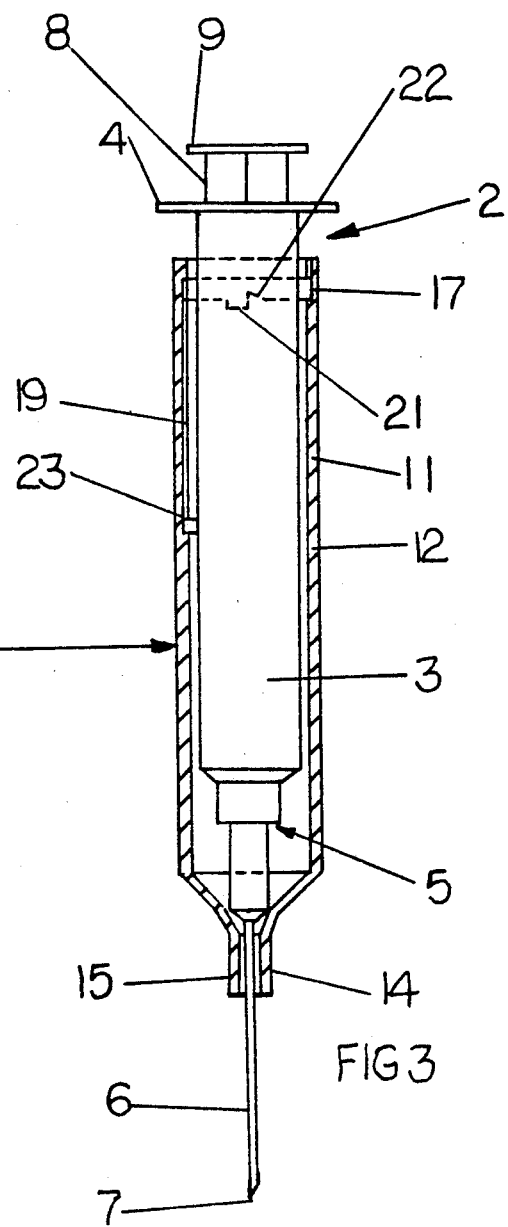
FIG. 3 is a view similar to FIG. 1 taken on the line 3—3 of FIG. 4, but illustrating the hypodermic needle rotated through 90° and adjusted relative to the sheath so as to enable the needle to be projected therefrom.
Figure 10:
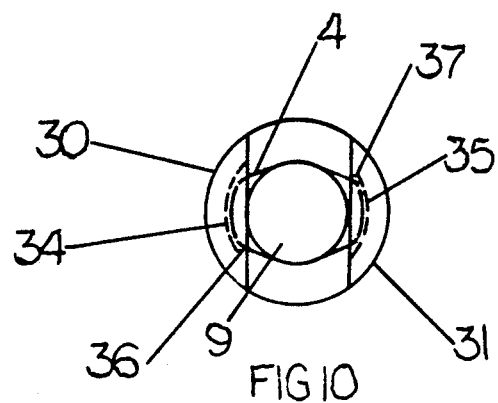
FIG. 10 is a top plan view of the device shown in FIG. 9.

In the positions of the parts shown in FIG. 1, the hypodermic needle 1 and the sheath 10 may be rotated relatively to one another so as to locate the projection 23 in the axial groove 19, whereupon the hypodermic needle may be moved downwardly from the position shown in FIG. 1 to the position shown in FIG. 3 in which the needle 6 is projected beyond the tip 14 of the sheath 10 in condition for use. Engagement of the projection 23 with the shoulder 20 limits the extent of movement of the hypodermic needle 1 downwardly relative to the sheath 10.

Following use of the hypodermic needle to inject or withdraw fluid into or from a person, the hypodermic needle may be returned to the position shown in FIG. 1, thereby again positioning the needle 6 wholly within the confines of the sheath 10.

The length of the sheath 10 relative to the syringe 2 and the needle 6 is such that the fingers of the user may grip both the barrel 3 and the sheath 10 at positions remote from the tip 7 of the needle, thereby minimizing substantially the risk of inadvertently pricking the user or some other person. The rigidity of the sheath is sufficient to avoid collapse of the body 11 and bending of the needle 6.

In the embodiment disclosed in FIGS. 9–12, the protective sheath 25 comprises a tubular body 26 having an annular side wall 27 that terminates at one end in a conical section 28 joined to an annular extension 29. At its opposite ends the body 26 includes a pair of circumferentially spaced, diametrically opposed extensions 30 and 31. Adjacent the juncture of the extensions 30 and 31 with the body side wall 27 the extension 30 has a discontinuous, circumferential slot 32 in its inner surface and the extension 31 has a similar slot 33 in its inner surface. The extension 30 also has a discontinuous, circumferential slot 34 adjacent its opposite end and the extension 31 has a similar slot 35 adjacent its opposite end. The slot 34 has an abutment or shoulder 36 adjacent one end, but is open at its other end. The slot 35 has a shoulder or abutment 37 at one end and is open at its opposite end.

Figure 9:
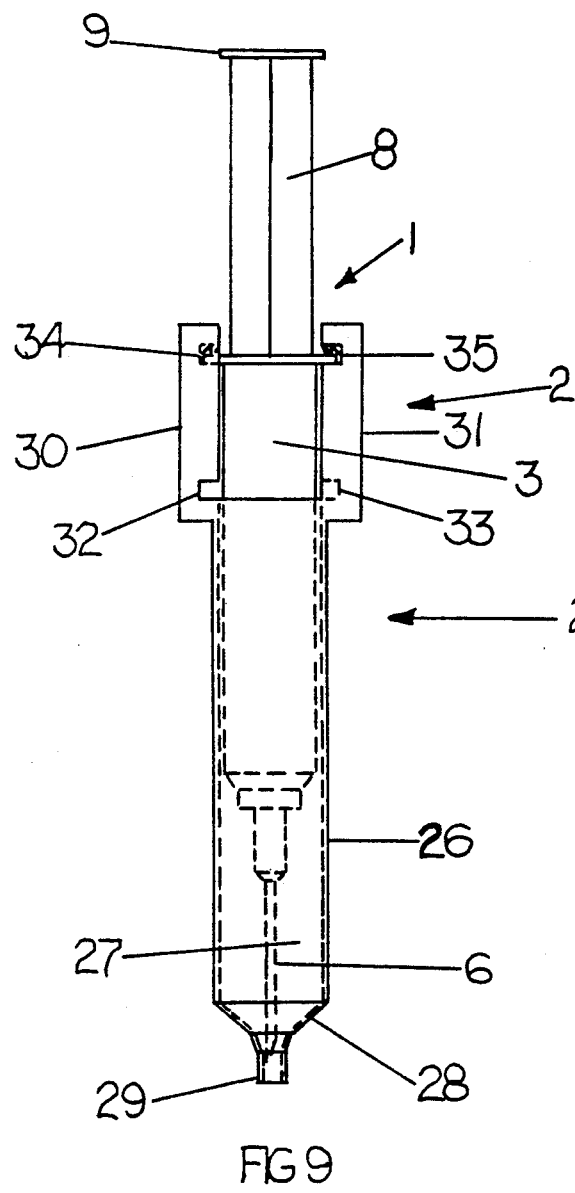
FIG. 9 is an elevational view illustrating a modified embodiment in a position in which the needle is encased in the sheath.

The bore of the sheath 25 is of such size as freely to accommodate the syringe 2 of the hypodermic needle 1 and is of such length as wholly to accommodate the needle 6 and a substantial portion of the syringe barrel 3, as is shown in FIG. 9.

Figure 13:
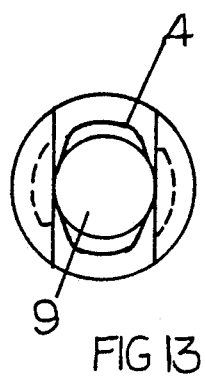
FIG. 13 is a view similar to FIGS. 10 and 12, but illustrating the syringe in an intermediate position between the positions shown in FIGS. 10 and 12.
Figure 12:
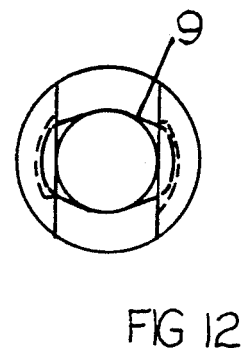
FIG. 12 is a top plan view of the device shown in FIG. 11.

To assemble the hypodermic needle 1 and the sheath 25, the needle 6 and the syringe barrel 3 are introduced to the body 26 from the open end thereof. The syringe is rotated relative to the sheath 25 so that the flange 4 may be accommodated between the extensions 30 and 31, as is indicated in FIG. 13. The syringe then may be moved farther into the sheath 25 until such time as the flange 4 is at the level of the slots 34 and 35, whereupon the syringe may be rotated counterclockwise from the position shown in FIG. 13 to the position shown in FIG. 10 until such time as the opposite ends of the flange engage the shoulders 36 and 37 at the ends of the slots 34 and 35, respectively. The syringe barrel and the needle 6 thus will be latched against axial movement in either direction relative to the sheath 25. The flange 4 constitutes one part of the latching means and the slots 34 and 35 constitute a second part of such latching means.

Figure 11:
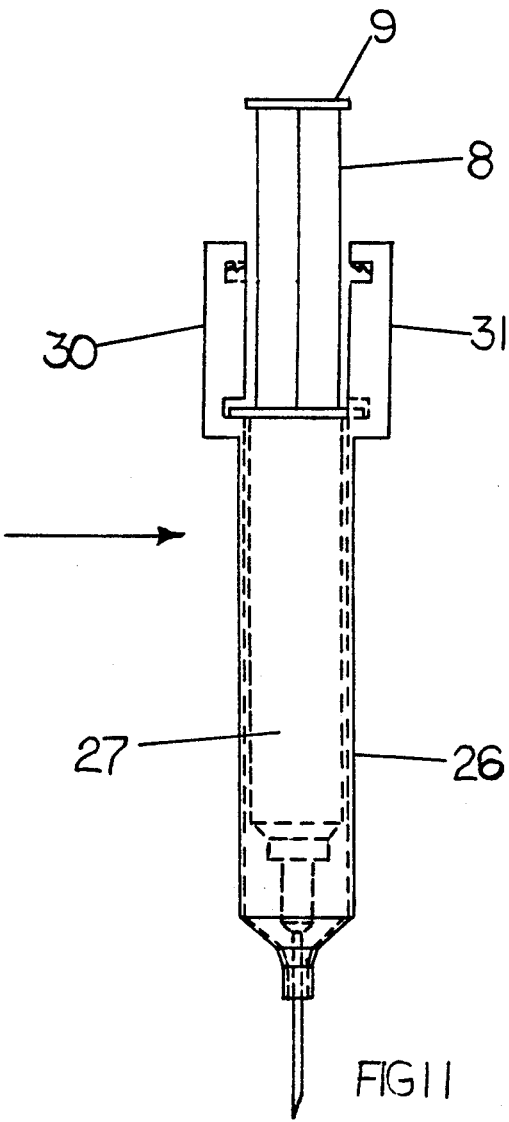
FIG. 11 is a view similar to FIG. 9, but illustrating the hypodermic needle rotated through 180° and the needle projected from the sheath.

When it is desired to make use of the hypodermic needle, the syringe is returned to the position shown in FIG. 13, following which the hypodermic needle may be moved downwardly relative to the sheath 25 from the position shown in FIG. 9 to the position shown in FIG. 11, whereupon the needle 6 is projected beyond the sheath. The syringe again may be rotated counterclockwise from the position shown in FIG. 13 to the position shown in FIG. 12 whereupon the opposite ends of the flange will enter the grooves 32 and 33 and move relative thereto until the flange tongues engage the shoulders at the corresponding ends of such grooves. The hypodermic needle thus will be latched in place in a position in which the needle is exposed for use. After use, the hypodermic needle may be returned to the position shown in FIG. 9.

In the embodiment shown in FIGS. 14–17 a protective sheath 40 comprises a tubular body 41 having an annular wall 42 open at one end and terminating at its opposite end in a concical section 43 joined to an annular tip 44. The cross sectional area of the body 41 is of such size as freely and slideably to accommodate the syringe 2 of the hypodermic needle 1 and its length is sufficient to accommodate the needle 6 and a substantial portion of the syringe barrel 3 so as to enable a portion of the syringe and the needle to be accommodated wholly within the sheath 40.

Latch means 45 is provided for latching the hypodermic needle and the sheath in selected positions of longitudinal adjustment and comprises a threaded screw shank 46 accommodated in a correspondingly threaded opening 47 formed in the wall 42 and having a knurled head 48 at its outer end by means of which the screw shank may be rotated from a position in which the screw shank bears against the barrel 3, as shown in FIG. 14, to a position in which the screw shank 46 is free from engagement with the barrel, as is shown in FIG. 16.

The sheath 40 is movable axially of the hypodermic needle 1 between positions in which the needle is wholly confined within the sheath and is projected beyond the sheath for use. Movement of the sheath to and from either of these positions can be effected while the operator's fingers are remote from the needle tip 7.

In the embodiment shown in FIGS. 18—21, the hypodermic needle 1A is the same as the hypodermic needle 1 with the exception that the syringe barrel 3A is provided with two pairs of external, axially spaced, circumferential flanges 49 and 50 forming a pair of circumferential relieved areas or grooves 51 and 52, respectively, and constituting parts of a latch.

The sheath 53 includes a second latch part or finger 58 which is slideably accommodated in an opening 59 in the body wall 55. The outer end of the finger 58 is pivoted as at 60 to an operating arm 61 which is pivoted between its ends at 62 to a bracket 63 secured to the body wall 55.

The bore of the sheath 53 is of such size as freely and slideably to accommodate the syringe barrel 3A and is of such length as to accommodate the needle 6 and a substantial portion of the syringe barrel.

In the positions of the parts shown in FIG. 18, the needle 6 is wholly accommodated within the sheath, and so is a substantial portion of the barrel 3A. The hypodermic needle is latched in this position by the finger 58 which projects radially and is accommodated in the groove 52 between the axially spaced flanges 50. However, the finger 58 may be withdrawn from the groove 52 by rocking the operating arm 61 to the position shown in FIG. 20, thereby enabling the hypodermic needle to be moved axially of the sheath 53 to the position shown in FIG. 20 in which the hypodermic needle 6 is projected for use. The hypodermic needle may be latched in this position by moving the latch finger 58 into the groove 51 between the flanges 49.

Again, movements of the sheath 53 between positions in which the needle 6 is retracted and projected may be effected without requiring the user's fingers to occupy a position close to the needle 6.

The sheath 65 shown in FIGS. 22 and 23 comprises a tubular body 66 having a closure wall 67 at one end. At its other end the body 66 is joined to an outwardly flared extension 68 which, in turn, is joined to an annular sleeve 69. The tubular portion 66 is of such internal diameter as freely to accommodate the needle and at least the lower part of the needle fitting 5, and the internal diameter of the sleeve 69 corresponds substantially to the outer diameter of the syringe body 3 so as to enable the sleeve and the syringe to have a friction fit which nevertheless enables relative sliding movement therebetween upon the application of adequate force.

In the positions in the parts shown in FIG. 22, the sheath 65 has been removed from the hypodermic needle 1, but it may be reassembled with the latter by permitting the needle 6 to pass through the sleeve 69, the portion 68, and the tubular portion 66 a distance sufficient to enable the sleeve 69 frictionally to accommodate and frictionally grip the sheath body 3. The frictional engagement between the body 3 and the sleeve 69 constitutes means for latching the sheath and the hypodermic needle in a position in which the needle 6 is wholly confined within the sheath. In handling the sheath 65 the user's fingers will engage the extension 68, thereby protecting the user from the needle.

The sheath 70 shown in FIGS. 24 and 25 has a tubular portion 71 terminating at one end in a closed end wall 72 and being joined at its opposite end to an outwardly flaring extension 73 terminating in an annular, extending grooved section 74. The section 74 is joined to an outwardly flaring section 75 which in turn is joined to an annular sleeve 76 which is fixed at one end of a funnel-like inlet 77. The portions 71, 73, and 74 of the sheath 70 are adapted to accommodate the needle 6, the fitting 5, and the adjacent portion of the syringe barrel 3, respectively, whereas the sleeve 76 is of such size as snugly and frictionally to accommodate the adjacent portion of the barrel. The inlet 77 extends radially beyond the barrel 3.

In the positions of the parts shown in FIG. 24, the sheath 70 is removed from the hypodermic needle 1, but may be assembled with the latter by movement relative thereto in such direction as to enable the needle 6 to be accommodated in the tubular portion 71 of the sheath. The inlet 77 simply serves as a guide to facilitate the application of the sheath 70 to the hypodermic needle 1. In the assembled condition of the parts, the frictional engagement between the sleeve 76 and the barrel 3 constitutes releasable latch means for maintaining the barrel and the sheath assembly.

During the movments of the sheath 70 to and from its assembled relation with the hypodermic needle, the fingers of the user engage the grooved section 74 and are protected at all times from engagement with the tip of the needle.

This disclosure is representative of preferred embodiments of the invention, but is intended to be illustrative rather than definitive thereof. The invention is defined in the claims.

I claim:

1. A hypodermic syringe comprising a tubular barrel having at one end an outwardly extending flange and at its other end a needle extending in one direction longitudinally of said barrel in prolongation thereof, said needle terminating at its distal end in a free tip; a sheath having an annular body of such length as to accommodate therein said needle in its entirety and at least a portion of said barrel, said portion of said barrel and said body being relatively rotatable and axially slideable; and a latch keeper carried by said body and extending axially thereof in a direction opposite that in which said needle extends from said barrel, said latch keeper having a circumferentially extending groove therein for the removable and slideable accommodation of said flange, said groove and said flange being of such relative circumferential lengths that said flange is movable in response to relative rotation of said barrel and said body between a first position in which said flange is accommodated in said groove thereby preventing relative axial movements of said barrel and said body and a second position in which said flange is clear of said groove thereby enabling relative axial movements of said barrel and said body a distance sufficient to extend said needle tip beyond said sheath.

2. The hypodermic syringe according to claim 1 wherein said latch keeper has a second annular groove axially spaced from the first mentioned groove for the accommodation of said flange when the latter is in said second position, thereby preventing relative axial movements of said barrel and said body.

3. The hypodermic syringe according to claim 1 wherein said groove has a stop defining one end of said groove and against which said flange may seat to limit relative rotation in one direction of said barrel and said body.

4. The hypodermic syringe according to claim 1 wherein said latch keeper comprises a pair of circumferentially spaced members each of which has said groove therein, said flange being less than 360° in circumferential length, and said members being spaced apart a distance sufficient to accommodate said flange therebetween when said barrel and said body are in said second position.

* * * * *